US006973156B2

(12) United States Patent
Sokolov

(10) Patent No.: US 6,973,156 B2
(45) Date of Patent: Dec. 6, 2005

(54) METHOD AND APPARATUS FOR RECONSTRUCTION OF THE ATTENUATION DENSITY OF AN OBJECT FROM X-RAY PROJECTION IMAGE DATA

(75) Inventor: Skiff Sokolov, Lidingö (SE)

(73) Assignee: XCOUNTER AB, Danderyd (SE)

(*) Notice: Subject to any disclaimer, the term of this patent is extended or adjusted under 35 U.S.C. 154(b) by 72 days.

(21) Appl. No.: 10/790,064

(22) Filed: Mar. 2, 2004

(65) Prior Publication Data
US 2005/0152505 A1    Jul. 14, 2005

(30) Foreign Application Priority Data
Jan. 13, 2004    (SE) .................. 0400045

(51) Int. Cl.[7] .............................................. A61B 6/03
(52) U.S. Cl. ........................................ 378/4; 378/901
(58) Field of Search ................... 378/4, 8, 15, 901

(56) References Cited

U.S. PATENT DOCUMENTS

| | | | | |
|---|---|---|---|---|
| 5,546,472 | A | * | 8/1996 | Levin .................. 382/131 |
| 6,307,909 | B1 | | 10/2001 | Flohr et al. |
| 2003/0190066 | A1 | * | 10/2003 | Boas et al. ............ 382/131 |

OTHER PUBLICATIONS

Townsend, "Image Reconstruction for Medical Applications", Advances in computer graphics VI Images: Synthesis, Analysis and Interaction, Sep. 4-7, 1990.

Baytas, "The projection map interpolation in parallel beam gammaray computed tomography", Applied Radiation and Isotopes 51 (1999) 717-724 AN 6457027.
Search Report.
Godfrey et al., Practical strategies for the clinical implmentation of matrix inversion tomosynthesis (MITS), Physics of Medical Imaging, Proceedings of SPIE vo., 5030, 2003, pp379-390.
Wu et al., "Tomographic mammography using a limited number of low-dose cone-beam projection images", 2003 AM. Assoc. phys. Med., pp 365-380.

* cited by examiner

Primary Examiner—David V Bruce
(74) Attorney, Agent, or Firm—Harness, Dickey & Pierce PLC

(57) ABSTRACT

A method for reconstruction of object attenuation density ($S(x,y,z)$) from X-ray projection image data values ($V(p_q)$) comprises the steps of: representing (11) the object attenuation density by a sum of predetermined continuous harmonics ($H_{ijk}(x,y,z)$) with unknown coefficients ($a_{ijk}$); relating (12) each of the projection image data values to an integral ($S(p_q)$) of the object attenuation density, and thus to a corresponding sum of sums ($a_{ijk}*H_{ijk}(p_q)$) of the predetermined continuous harmonics with unknown coefficients; determining (13) the unknown coefficients ($a_{ijk}$) from the above relation; and reconstructing (14) the object attenuation density by said sum of predetermined continuous harmonics with said determined coefficients. The spatial three-dimensional object attenuation density is found as a continuous function with uniform resolution over all its volume and is shown as a solid three-dimensional body, which can be cut in arbitrary way and shown in continuous motion.

18 Claims, 1 Drawing Sheet

METHOD AND APPARATUS FOR RECONSTRUCTION OF THE ATTENUATION DENSITY OF AN OBJECT FROM X-RAY PROJECTION IMAGE DATA

FIELD OF THE INVENTION

The invention relates generally to X-ray imaging, and more specifically to a method and an apparatus, respectively, for reconstruction of the attenuation density of an object from X-ray projection image data, to a computer program product for performing the reconstruction method when run on a computer, and an X-ray detector apparatus comprising an X-ray detector, a display unit and the reconstruction apparatus. The invention is preferably, but not exclusively, suited to be used in tomosynthesis examinations.

BACKGROUND OF THE INVENTION AND RELATED ART

Widely used reconstruction methods in X-ray tomosynthesis imaging replace the reconstruction of attenuation density values of a real continuous object by the reconstruction of attenuation density values of a discontinuous model of the object consisting typically of a number of spatially separated planes, in which all structure is concentrated.

Such replacement reduces the problem of reconstruction to the solution of an algebraic system of equations, which link the pixel values of images detected to pixel values on different object planes. These equations are solved either exactly (in rare cases of very small images), or approximately by various successive approximations methods using, e.g., differences between original and back-projected images for calculating corrections, and various simplifications of equations. There is a large literature on the subject, see e.g. D. J. Godfrey, A. Rader, J. T. Dobbins III. Practical strategies for the clinical implementation of matrix inversion tomosynthesis (MITS), Medical Imaging 2003, Proc. of SPIE Vol. 5030(2003), p. 379–390, and Tau Wu, D. B. Kopans, R. H. Moore, J. W. Eberhard, B. Opsahl-Ong, L. Miklason, M. B Williams, Tomographic mammography using a limited number of low-dose cone-beam projection images. Med. Phys. 30(3), 365–380, 2003, and references therein.

SUMMARY OF THE INVENTION

A first important limitation of the prior art discontinuous model is that the number of reconstructed surfaces is strictly restricted. In the most common case, when the reconstruction surfaces are planes of the same size as the detected images, the number of planes is limited by the number of images. Otherwise, the number of unknowns will exceed the number of equations, and they could not be solved.

The restricted small number of reconstructed planes has two effects. Firstly, sharpness of details of the object visible on reconstructed planes depends on their position with respect to the nearest plane. If the detail of the object happens to lie in space between two planes, far from each plane, it is smeared and easily obscured by better visible details that happen to lie nearer the plane. Secondly, the set of widely spaced planes do not look as a three-dimensional body, and this limits obviously recognition of visible details. Narrow elongated details intersecting several planes look as unrelated spots on several planes, and it is difficult to decide whether they belong to independent small objects, or to sections of one longer object.

A second limitation is that the noise and image defects are strongly enhanced due to poor quality of matrices associated with equations. To improve the signal-to-noise quality of the reconstructed images, one is forced to reduce further the number of reconstructed planes, and to filter out the noise to the cost of a deteriorated spatial resolution.

A third limitation is the large computing time needed for reconstruction, since the computing time is proportional to the number of iterations performed. Often up to 20 iterations are used.

An object of the invention is therefore to provide a method and an apparatus, respectively, for reconstruction of object attenuation density values from X-ray projection image data, by which the problems and limitations of the prior art approach described above are avoided, or at least heavily reduced.

In this respect there is a particular object to provide such a method and such an apparatus, wherein sharpness of details of the object in the reconstructed attenuation density do not depend on their position with respect to some model plane.

A further object of the invention is to provide an algorithm, which is mathematically stable.

A still further object of the invention is to provide such a method and such an apparatus, wherein details in the reconstructed attenuation density are not smeared and obscured by other details.

A yet further object of the invention is to provide such a method and such an apparatus, wherein narrow elongated details are easily recognized and visualized in the reconstructed attenuation density.

A still further object of the invention is to provide such a method and such an apparatus, which are uncomplicated and can produce high-quality visualizations of object attenuation density with high spatial resolution, high signal-to-noise ratio, high dynamic range, high image contrast, and low noise from overlaying tissue.

A yet further object of the invention is to provide such a method and such an apparatus, which need less computing time than prior art methods and apparatuses need.

A still further object of the invention is to provide such a method and such an apparatus, which are reliable, accurate, and inexpensive.

These objects, among others, are attained by methods and apparatuses as claimed in the appended claims.

The inventor has found that by using a method for reconstruction of the attenuation density of an object from X-ray projection image data values comprising the steps of (i) representing the attenuation density of the object by a sum of predetermined continuous harmonics with unknown coefficients; (ii) relating each of the X-ray projection image data values to an integral of the attenuation density of the object, and thus to a corresponding sum of sums of the predetermined continuous harmonics with unknown coefficients; (iii) determining the unknown coefficients from the relations between each of the X-ray projection image data values and the respective corresponding sum of sums of the predetermined continuous harmonics with unknown coefficients; and (iv) reconstructing the attenuation density of the object by the sum of predetermined continuous harmonics with the determined coefficients, all the above objects are attained.

Preferably, different ones of the predetermined continuous harmonics, which may be e.g. Newton polynomials, spline interpolating functions, Fourier harmonics, Bessel functions, or Green functions, representing different spatial frequencies of the attenuation density of the object can be used, and the number of them is less than the number of the X-ray projection image data values.

Still preferably, the X-ray projection image data values are obtained from X-ray absorption/transmission measurements, and the integrals of the attenuation density of the object are each an integral along a straight line along which X-rays traveled to produce the related X-ray projection image data value.

The object attenuation density is reconstructed as a continuous three-dimensional function and the result of the reconstruction is a three-dimensional continuous body with uniform resolution all over the body. Two-dimensional cuts of the reconstructed body can be made in any arbitrary way and, in particular, cuts may be made at any depth and at any projection angle. The attenuation density will be visualized with the same or similar sharpness in each arbitrarily chosen cut. The cutting planes and the body itself can be shown in continuous motion including rotation.

Selection of the coefficients, which are calculated and used, is done on basis of their estimated signal-to-noise ratio or, equivalently, by setting relevant limitations on quality of matrices associated with harmonics used.

According to further aspects of the present invention, a computer program product and a reconstruction apparatus are provided for performing the above method.

According to still a further aspect of the present invention, an X-ray examination system is provided comprising the above reconstruction apparatus, an X-ray detector provided to produce the X-ray projection image data values, and a display unit for displaying results of the reconstruction.

Further characteristics of the invention, and advantages thereof, will be evident from the detailed description of preferred embodiments of the present invention given hereinafter and the accompanying FIGS. 1–3, which are given by way of illustration only, and thus are not limitative of the present invention.

DESCRIPTION OF PREFERRED EMBODIMENTS

Figure 1:
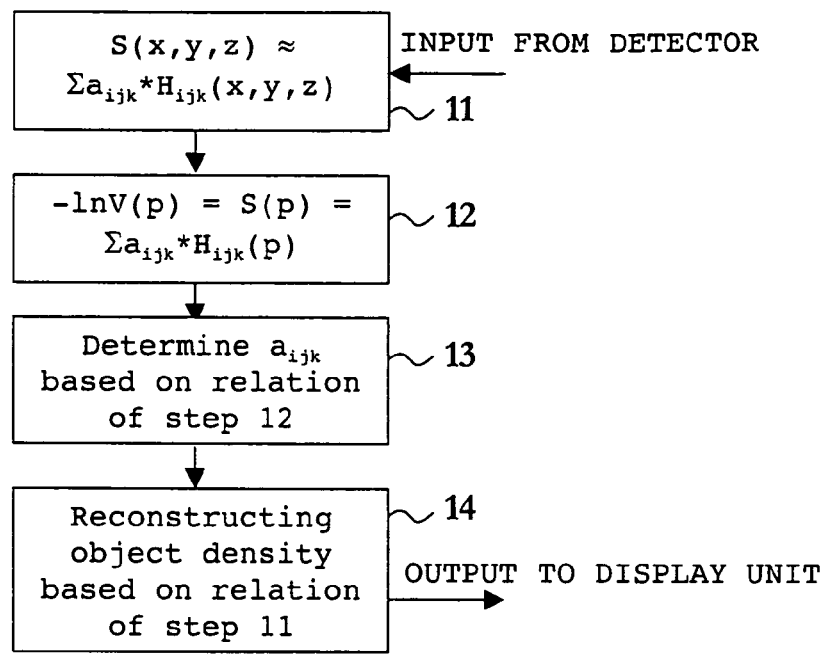
FIG. 1 is a schematic flow scheme of a method according to a preferred embodiment of the present invention.

A method according to a preferred general embodiment of the present invention is disclosed below with reference to FIG. 1. The reconstruction of continuous three-dimensional unknown object attenuation density $S(x,y,z)$ begins after having received input data of the X-ray examination method, which has been performed, such as the maximum size of the object, the number of pixel values in one or two dimensions, and the number of different angles, in which detection is performed, and naturally the X-ray projection image data values, i.e. the pixel values $V(p_q)$ at pixel point $p_q$ on image q, themselves.

Generally, a number of two-dimensional X-ray images taken at different angles provides for the reconstruction of object attenuation density in three dimensions, whereas a number of one-dimensional X-ray images taken at different angles (in the plane of the one-dimensional images) provides for the reconstruction of object attenuation density in a plane, only. The present invention is applicable to both kind of examination, but in the following a general approach for reconstruction of three-dimensional object attenuation density is disclosed. It is appreciated that the man skilled in the art would modify this approach (simply by dropping one dimension) to provide object attenuation density in the latter kind of examination.

The reconstruction method begins, in a first step 11, by approximately representing the unknown function $S(x,y,z)$ as a sum of continuous harmonics $H_{ijk}(x,y,z)$ with unknown coefficients aijk, i.e.

$$S(x,y,z) \approx \Sigma a_{ijk} * H_{ijk}(x,y,z)$$

Different ones of the continuous harmonics $H_{ijk}(x,y,z)$ represent different spatial frequencies of the object attenuation density $S(x,y,z)$. Typically, the index i runs from 0 to the number N of different angles, at which X-ray imaging is performed, and the indexes j and k runs from 0 to the number of pixel values in respective direction of the detected X-ray images. Typically, each of the indexes denotes spatial frequencies from zero frequency to the maximum frequency detectable (which is given by the number of angles, and number of pixel values in the respective directions of the detected images) in the three perpendicular directions of space. These spatial frequencies are related to each other, and typically only half or less than half of the product $i*j*k$ of harmonics are actually used in the reconstruction. Typically, $I \leq j$ in the low-frequency region $j<N$ and $I<1$ at some part of high-frequency region of large j.

Then, each of the pixel values $V(p_q)$, q=1, 2, 3, ... of the detected X-ray object images are, in a step 12, related to an integral $S(p_q)$ of unknown function $S(x,y,z)$. The integral $S(p_q)$ is thus a sum of coefficients $a_{ijk}$ multiplied by similar sums $H_{ijk}(p_q)$ of $H_{ijk}(x,y,z)$. These relations give a system of linear equations of the form:

$$-\ln(V(p_q)) = S(p_q) \approx \Sigma_{ijk} a_{ijk} * H_{ijk}(p_q) = \Sigma_{ijk} \Sigma_p a_{ijk} * H_{ijk}(x,y,z)$$

where values $a_{ijk}$ are unknown and where possible normalization corrections have been omitted.

In the simplest case the integral $S(p_q)$ is the integral along a straight line along which X-rays traveled to produce the related X-ray projection image data value.

It shall be appreciated that the selection of kind and of the number of harmonics that shall be used, as well as the computation, analytical or numerical computation, whichever is the simplest, of the sums $H_{ijk}(p_q)$ of $H_{ijk}(x,y,z)$ can be made prior to the X-ray examination provided that the setup data of the X-ray examination has been determined.

Then, in a step 13, the unknown coefficients $a_{ijk}$ are calculated from these linear equations, and finally, in a step 14, the attenuation density of the object $S(x,y,z)$ is reconstructed by the sum of predetermined continuous harmonics with the determined coefficients, $\Sigma a_{ijk} * H_{ijk}(x,y,z)$.

The object attenuation density $S(x,y,z)$ can be computed at any desirable space point $P(x,y,z)$. Computed data is then sent to a display unit for visualization of the object attenuation density $S(x,y,z)$.

A three-dimensional attenuation density picture of the entire object may be displayed, a cut through the object in any plane can be shown, and three-dimensional motion pictures can be generated.

Of course, the number of coefficients $a_{ijk}$, which can be found, cannot exceed the total number of X-ray projection image data values or pixel values $p_q$, but the number of points, where the object attenuation density can be computed is not limited. Only the spatial resolution of the object attenuation density is limited.

As usual, the spatial resolution depends on the set of positions of the object for which X-ray images are taken, and is often anisotropic (dependent on direction), but it does not depend on the space point P(x,y,z) to any larger extent.

The choice of harmonics $H_{ijk}(x,y,z)$ and coordinates x,y,z, e.g. Cartesian, cylindrical, etc., can be made arbitrarily, but in many cases a few or a single kind of harmonic is to be preferred. The harmonics may be Newton polynomials, some spline interpolating functions, Fourier harmonics, Bessel functions, Green functions, etc. By making an optimum choice, using knowledge of symmetries of object positions, etc., greatly simplifies the calculation of $a_{ijk}$ and the control over signal-to-noise ratio of the object attenuation density S(x,y,z).

Preferably, the X-ray projection image data values are tomosynthesis data values, and the reconstruction method is a method for tomosynthesis reconstruction. However, the invention is applicable to any kind of X-ray projection image data values, such as e.g. tomographic, PET, or SPECT data values.

The total number of harmonics used to represent the object attenuation density determines the spatial resolution obtainable. This in turn depends on (i) the scanning step or pixel size in the detected images; (ii) the number of different angles, at which images are detected, (iii) the angular spread of these angles; (iv) the radiation dose permitted, i.e. the maximum number of X-ray photons that can be used in the measurement; and (v) the presence of additional noise in the image, e.g. electronic noise or noise from scattered X-rays.

An advantage of the present invention is that it makes it possible to accurately select the region in the space of indexes i,j,k, where the coefficients $a_{ijk}$ are larger than noise in these coefficients. The coefficients $a_{ijk}$ should be calculated and used in the sum of functions $\Sigma a_{ijk}*H_{ijk}(x,y,z)$ representing the object attenuation density S(x,y,z) only if signal-to-noise ration in these coefficients being higher than a selected signal-to-noise threshold value. Coefficients $a_{ijk}$, where noise dominates, and $a_{ijk}$ should be omitted. Such selection is much more efficient for image improvement than noise filtration used in prior art reconstruction methods, and give sharper and less noisy images.

Figure 2:
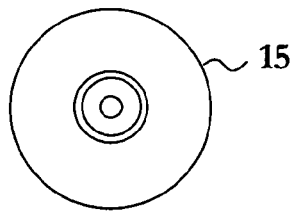
FIG. 2 illustrates a storage medium storing a computer program product for performing any of the methods of the present invention when run on a computer.

FIG. 2 illustrates a storage medium storing a computer program product loadable into the internal memory of a computer, comprising software code portions for performing any of the reconstruction methods of the present invention when run on a computer.

Figure 3:
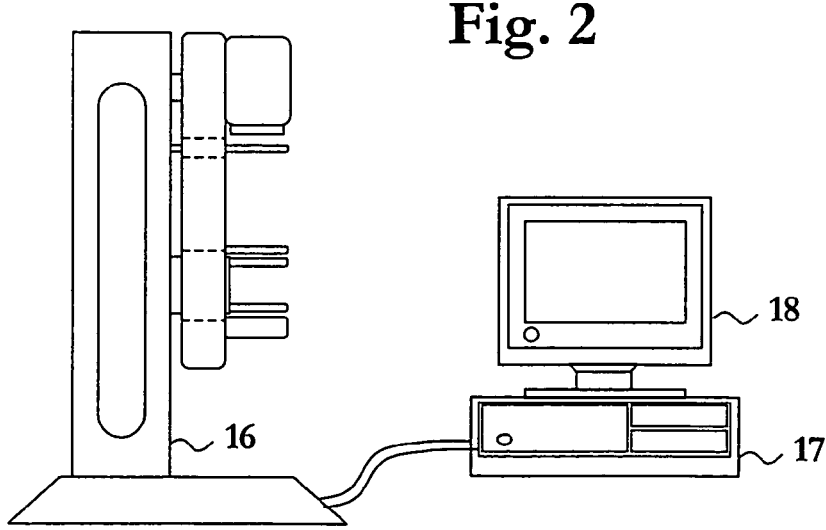
FIG. 3 illustrates an X-ray examination system, in which the present invention is implemented.

FIG. 3 illustrates an X-ray examination system, in which the present invention is implemented. The system comprises an X-ray detector 16 provided to produce the X-ray projection image data values needed for reconstruction; a reconstruction apparatus 17 including means provided to perform any of the reconstruction methods of the present invention; and a display unit 18 for displaying object attenuation density values. The reconstruction apparatus 17 is provided (i) to receive the X-ray projection image data values from the X-ray detector 16, and (ii) to supply data regarding the attenuation density of the object to the display unit 18.

The details of the reconstruction process of the present invention in order to determine the coefficients $a_{ijk}$ depend on the set of X-rayed object positions r, but the method consists basically of a summation over of both sides of (1) with some functions $G_{lmnr}(p_q)$ that may coincide with functions H or with their complex-conjugate, and a solution of the obtained system of K linear equation for K unknowns coefficients $a_{ijk}$.

With a suitable choice of the harmonics $H_{ijk}(x,y,z)$ and the functions $G_{lmnr}(p_q)$, the equation system for $a_{ijk}$ splits into independent (or weakly coupled) subsystems of small number of equations, which are easily solvable. An example of such method is described below in a detailed example embodiment of the present invention. Tests in comparable cases have shown that the present invention is more tolerant to the absence of part of data and is faster than the traditional plane-like reconstruction method.

EXAMPLE EMBODIMENT OF THE PRESENT INVENTION

A typical tomographic problem, which occurs when the object is compact and surrounded by uniform margins, and its shadow is smaller than the size of the images taken, is considered. As is usual in transmission tomography, the attenuation density S(x,y,z) will be interpreted as the probability density to lose a photon on its way to the detector due to photoelectric absorption and scattering in the object.

The optimal choice of coordinates x,y,z and harmonics $H_{ijk}(x,y,z)$ depends of the type of the motion of the object with respect to X-ray source during the X-ray transmission detection. The embodiment assumes as an example that the object is linearly translated between X-ray exposures, or, which is equivalent, the X-ray source is linearly shifted between exposures. Let this shift be in Y direction.

In this case, it is advantages to use, instead of Cartesian coordinates, pyramidal coordinates x, y, z such the planes x=constant and y=constant pass through the point of the X-ray source X=Y=Z=0 and are non-parallel, unlike planes X=constant and Y=constant that are parallel. In pyramidal coordinates x, y, z, all points of the ray, from the X-ray source to the image pixel (detector element) p(x,y) in plane Z=Z0 have the same coordinates x and y.

The relation between Cartesian and pyramidal coordinates is $$X=x*Z/Z0, \quad Y=y*Z/Z0, \quad Z=z$$

where Z0 is Z of the plane of detector (of image). The attenuation density of the object in Cartesian coordinates D(X,Y,Z) is related to function S(x,y,z) by $$S(x,y,z)=D(X*Z/Z0,Y*Z/Z0,Z)$$

Before reconstruction, it is convenient to pass from normal image intensity V(x,y) to normalized logarithmic image value P(x,y), corrected to both $1/d^2$ intensity law for divergent rays, where d is the distance from the focal spot, and coefficient $$ds/dz=\sqrt{(x^2+y^2+z^2)}/z$$

arising in the integration along the ray, see Appendix below. Explicitly, P is connected to V by $$P(x,y,r)=-\ln(V(x,y,r)*(x^2+y^2+z0^2)/ \quad Vmax*z0^2)/\sqrt{1+(x^2+y^2)/z0^2)},$$

where also the index r is added to distinguish images taken at different translations t(r) of the object.

If the detector is well collimated and scattered photons do not contribute to the detected image, the relation between image value and object attenuation density is $$P(x,y,r)=\mathrm{INT}(z:0-Z0)S(x,y-t(r)*z/Z0,z)*dz \qquad (1)$$

where INT(z:0–Z0) denotes the integral over z from 0 to z0.

In this case, variable x (in pyramidal coordinates) completely separates, and the tomographic problem reduces to a two-dimensional reconstruction problem in the yz plane.

If collimation is not good and scattering photons contribute to $P(x,y,r)$, their contribution may be taken into account in the frame of transmission tomography approximately by certain smearing factor $w(d^2,z)$ in the integral expression as follows $$P(x,y,r)=\text{INT}(u,v,z:0-Z0)S(x+u,y+v-t(r)*z/Z0,z)*w(u^2+v^2,z)*du*dv*dz \quad (2)$$

where integration over u and v is done over the region where w is significant. The bell-shaped function w can be found from calibration measurements with suitable phantoms and should be fixed before reconstruction of S.

Basic elements of reconstruction method in cases (1) and (2) are similar. We continue here with easier case (1), and the more extensive formulas for case (2) are found in the Appendix below.

Since object motion is a linear translation and the proper functions of translation group are complex exponents, we choose functions H for the expansion in yz plane (of size sy,sz) in exponential form $$H_{fg}(y,z)=\exp(i*f*y*Cy)*\exp(i*g*z*Cz)$$

where $Cy=2*pi/sy$, $Cz=2*pi/sz$

Substitution of $$S(x,y,z)=\Sigma_{fg}a_{fg}(x)*H_{fg}(y,z) \quad (3)$$

(when frequencies f and g may be both negative and positive) into Eq. (1) gives $$P(x,y,r)=\Sigma_{fg}[a_{fg}(x)*\exp(i*f*y*Cy)*\exp(i*\text{pi}*(g-f*t(r)/Z0))*\sin C(\text{pi}*(g-f*t(r)/Z0))*Z0/2] \quad (4)$$

where function sin C is defined as $\sin C(x)=\sin(x)/x$.

The Fourier expansion of P in y direction $$P(x,y,r)=\Sigma_f F(x,f,r)*\exp(i*f*y*Cy)$$

where F is a Fourier transform, separates the variable f (turns it into parameter like x) and reduces Eq. (4) to a one-dimensional reconstruction problem $$F(x,f,r)=\Sigma_g a_{fg}(x)*\exp(i*\text{pi}*(g-f*t(r)/Z0))*\sin C(\text{pi}*(g-f*t(r)/z0))*z0 \quad (5)$$

containing rmax equations. Evidently, not more than rmax coefficients $a_g$ (for fixed f and z) can be found from Eq. (5). Actually, the maximal number gmax of harmonics in z direction that can be found, is smaller and depends on frequency f in the y direction.

For example, at f=0, only one harmonic g=0 may be found, since the right hand side of Eq. (4) gets rid the dependence on r at f=0, and only one independent equation remains. Besides, even if a certain number of harmonics can be found algebraically, calculated coefficients $a_g$ may have no sense due to catastrophic amplification of noise contained in V, P, and F. Noise limitations are stronger than algebraic ones.

Next step of reconstruction is to reduce Eq. (5) to equations for smaller number of harmonics that contain acceptable noise. To come to weakly coupled equations for $a_g$, we sum both sides of Eq. (5) over r with functions $$G_g(x,f,r)=\exp(-i*\text{pi}*(g-f*t(r)/Z0))*\sin C(\text{pi}*(g-f*t(r)/Z0))$$

which are, up to a scale, complex conjugate to functions in the right-hand-side of Eq. (5). Summation gives the system of equations $$\Sigma_g M_{kg}*a_g=J_k \quad (6)$$

where symmetric matrix M depends on parameter f $$M_{kg}(f)=\Sigma_r \sin C(\text{pi}*(k-f*t(r)/Z0))*\sin C(\text{pi}*(g-f*t(r)/Z0))$$

and $$J_k=\Sigma_r G_k(x,f,r)*F(x,f,r)$$

Matrices M do not depend on x and r and their quality as function of f and gmax is analyzed once before solution of Eqs. (6).

The choice of gmax(f) is generally made so as to use only invertible positive-definite matrices M and to retain in S only the coefficients $a_g$ with acceptable signal-to-noise ratio.

The signal $a_g$ is the property of the object and does not depend on the choice of gmax. But the noise in $a_g$ (the dispersion of $a_g$) is proportional to squared elements of inverse matrix $N=1/M$, which depend on the choice of gmax. To find correct gmax(f), one may calculate the dispersion of $a_g$ from the noise contained in detected images as function of gmax, and then set gmax as function of f and, possibly of x so as to achieve a desired signal-to-noise ratio in the reconstructed attenuation density S.

Practically, accurate noise estimation is not needed. Instead, it is sufficient, for each frequency f, to check that $\det(M)>0$ and to compute an inverse quality ("badness") b of matrix M $$b=\max_i M_{ii}*N_{ii}$$

as function of gmax. The dimensionless value b has the meaning of (maximum) noise amplification factor, which is of the growth of relative noise in $a_g$ compared to the relative noise in J. The value b grows fast (exponentially) with gmax, so a rough limitation of b by some number B of the order of two gives already a reasonable estimate of gmax. A better estimate of gmax gives the inequality $$b(f,\text{gmax})<B*(\text{abs}(f)+1)/f\text{max}$$

based on the observation that all image Fourier harmonics $G_g$ have usually approximately the same dispersion, and the standard error of J is approximately proportional to frequency f. The constant B fixes the trade-off between the focal depth (resolution in z direction) and the noisiness of the reconstructed attenuation density S.

After fixation of gmax(f), the Eqs. (6) are solved $$a_g=\Sigma_k N_{gk}*J_k \quad (7)$$

for all f and x, and the result is used to calculate the function S by Eq. (3) at all desirable points x,y,z.

Optionally, the function S can be additionally filtered in y and z directions by multiplying amplitudes $a_{fg}(x)$ by some function $L(f,g)$ suppressing, for example, high frequencies or manifestation in S of some defects of the initial images.

Next step is to represent the determined function $S(x,y,z)$ as three-dimensional body. Eq. (3) gives evidently a possibility to compute the attenuation density S on any plane or other surface, or cut of the object, and possibilities to make visualizations wherein plane cuts are move continuously, or wherein the object is rotated in space. Actually any possible way to visualize an analytically given three-dimensional function is may be performed.

The resolution of function S in z direction is limited by the number rmax of body images and usually is about dozen times worse then in x and y directions. The important feature of function S is that, in spite of poorer resolution in the z direction, its inclined cuts are almost as sharp as z planes, provided that cuts are not too close to vertical planes.

The only practical inconvenience with the function S stored as coefficients $a_{fg}$ in Eq. (3) is the considerable time needed to calculate functions H at points in the cut plane that will be shown on the screen. It can be avoided in several ways.

One of simple ways to compute quickly various cuts and transformations of S without recalculation of exponents, is first to calculate S at all x and y and at sufficiently many (of the order of several hundreds) planes z=constant, and store the result in a three-dimensional array S of size sx, sy, sz. Calculation of S can be done easily, since calculation of H at nodes of regular grid needs the forehand calculation of only sy+sz values of exponents. After that, the calculation of pixels in a cut plane reduces to selection of nodes x, y, z, closest to the points X, Y, Z, that should be displayed on the screen, and, possibly, to interpolate between these nods.

If the array S is larger than the computer memory, it can be stored externally as several slices of the size, fitting into memory, and the list of required cut points X, Y, Z can ordered so that the retrieval of corresponding node values would require to load slices of S into memory only ones, one by one, in natural order.

Fast calculation of cuts and other views makes it possible to select them interactively, by means of keyboard and mouse commands.

The detailed three-dimensional table S of attenuation density values opens the possibility for computer analysis of three-dimensional structures within the tomographed object, which was successfully attempted in high-resolution magnetic nuclear resonance tomography (MRI), but was not up to now possible in transmission tomography. For example, computer analysis can extract from three-dimensional mammograms the spatial pattern of micro-calcifications, which is much more informative, than flat projection and which cannot be extracted from a few distant planes determined by the prior art methods.

Appendix

The physical relation between attenuation density S and pixel value v when scattered photons are lost is $$v=(C/R^2)*\exp(-INT\_(path\ s)S(x,y-t,z)ds),$$

where INT_(path s) means the integral along the path of X-ray, C is the product of source intensity (per sterradian), by exposition time, by pixel area, and by detector efficiency, R is the distance from source to detector pixel, and ds=dz R/z0. Replacing absolute normalization constant C by more convenient relative normalization Vmax*z0^2, where Vmax is the pixel value at x=y=0 in calibration image without object, taking logarithm of both sides, and shifting all z-independent terms to the left-hand-side, we arrive at the Eq. (1).

In case when some scattered photons reach the detector, one sets $$S(x,y,z)=\Sigma_{kfg}a_{kfg}(x)*H_{kfg}(x,y,z)$$

$$H_{kfg}(x,y,z)=\exp(i*k*x*Cx)*\exp(i*f*y*Cy)*\exp(i*g*z*Cz)$$

Let scattering function w have the Gauss form $$w(u,v,z)=\exp(-(u^2+v^2)/(2*s(z)^2))/2*pi*s(z)^2$$

where s(z) sets the efficient size of the area around the ray connecting X-ray source and pixel, from where the photons reach the detector. Then $$INT(u,v)\exp(i*k*(x+u)*Cx)*\exp(i*f*(y+v)*Cy)*w*du*dv=\exp(i*k*x*Cx)*\exp(i*k*x*Cy)*W(k,f,z)$$

where $$W(k,f,z)=\exp(-(k^2+f^2)*s(z)^2/2).$$

The function sin C(q) is replaced by the function $$I(q,k)=INT(z)\exp(i*z*q)*W(k,f,z)dz$$

Equations for unknowns $a_{kfg}$ for different k and f are independent and are solved separately, as above for x and f.

The dependence of gmax(k,f) on k is weak, so it can be well approximated by gmax(0,f) found in the same way as above.

In case of good detector collimation $$s(z) \geq 0, I(q,k) \geq \sin C(q),$$

and expansion in x direction becomes superfluous.

What is claimed is:

1. A method for reconstruction of the attenuation density of an object from X-ray projection image data values, comprising the steps of:
   representing the attenuation density of said object by a sum of predetermined continuous harmonics with unknown coefficients;
   relating each of said X-ray projection image data values to an integral of the attenuation density of said object, and thus to a corresponding sum of sums of said predetermined continuous harmonics with unknown coefficients;
   determining said unknown coefficients from the relations between each of said X-ray projection image data values and the respective corresponding sum of sums of said predetermined continuous harmonics with unknown coefficients; and
   reconstructing the attenuation density of said object by said sum of predetermined continuous harmonics with said determined coefficients.

2. The method of claim 1 wherein different ones of said predetermined continuous harmonics represent different spatial frequencies of the attenuation density of said object.

3. The method of claim 1 wherein said predetermined continuous harmonics are any of Newton polynomials, spline interpolating functions, Fourier harmonics, Bessel functions, and Green functions.

4. The method of claim 3 wherein said predetermined continuous harmonics are selected to be of the kind, which minimizes the coupling of equations for given symmetries of object positions.

5. The method of claim 1 wherein said predetermined continuous harmonics is of a number, which is less than the number of said X-ray projection image data values.

6. The method of claim 1 wherein said predetermined continuous harmonics is of a number, which maximizes the signal-to-noise ratio of the reconstructed attenuation density of said object.

7. The method of claim 1 wherein said X-ray projection image data values are obtained from X-ray absorption or transmission measurements, and said integrals of the attenuation density of said object are each an integral along a straight line along which X-rays traveled to produce the related X-ray projection, image data value.

8. The method of claim 7 wherein said X-ray projection image data values are tomosynthesis data values, and said reconstruction is a tomosynthesis reconstruction.

9. The method of claim 7 wherein said X-ray projection image data values are tomographic, PET, or SPECT data values, and said reconstruction is a tomographic, PET, or SPECT reconstruction.

10. The method of claim 1 wherein each said sum of sums of said predetermined continuous harmonics is computed, numerically or analytically, prior to obtaining said X-ray projection image data values.

11. The method of claim 1 wherein said sum of predetermined continuous harmonics with unknown coefficients are selected depending on their estimated signal-to-noise ratio.

12. The method of claim 1 wherein said sum of predetermined continuous harmonics with unknown coefficients are selected depending on the quality of the matrices arising in the equations determining coefficients.

13. A method for reconstruction of the attenuation density of an object from X-ray projection image data values, comprising the steps of:

approximating the attenuation density $S(x,y,z)$ of said object by predetermined continuous harmonics $H_{ijk}(x,y,z)$ with unknown coefficients $a_{ijk}$ according to $S(x,y,z) = \Sigma a_{ijk} * H_{ijk}(x,y,z)$, where the number of said harmonics is lower than the number of said X-ray projection image data values;

relating each of said X-ray projection image data values $V(p_q)$ to the attenuation density of said object according to $-\ln(V(p_q) = S(P_q)$, $q=1, 2, 3, \ldots$, where $S(P_q)$ is a sum of attenuation density values of said object;

relating each of said X-ray projection image data values $V(P_q)$ to said harmonics according to $-\ln(V(P_q)) = \Sigma a_{ijk} * H_{ijk}(P_q)$ to form a linear equation system, where $H_{ijk}(P_q)$ is a sum of harmonics corresponding to said sum of attenuation density values of said object;

calculating the unknown coefficients $a_{ijk}$ by solving said linear equation system; and reconstructing the attenuation density of said object by calculating $S(x, y, z) = \Sigma a_{ijk} * Hi;k (x, Y, z)$.

14. The method of claim 13 wherein said X-ray projection image data values are obtained from X-ray transmission measurements, and said sums of attenuation density values $S(P_q)$, $p=1, 2, 3, \ldots$, are each a sum along a respective straight X-ray path from an X-ray source to a pixel of a detector, in which pixel the corresponding X-ray projection image data value was detected.

15. A computer program product loadable into the internal memory of a computer, comprising software code portions for performing the method of claim 1 when said product is run on said computer.

16. An apparatus for reconstruction of the attenuation density of an object from X-ray projection image data values, said apparatus comprising:

means provided to represent the attenuation density of said object by a sum of predetermined continuous harmonics with unknown coefficients;

means provided to relate each of said X-ray projection image data values to an integral of the attenuation density of said object, and thus to a corresponding sum of sums of said predetermined continuous harmonics with unknown coefficients;

means provided to determine said unknown coefficients from the relations between each of said X-ray projection image data values and the respective corresponding sum of sums of said predetermined continuous harmonics with unknown coefficients; and means provided to reconstruct the attenuation density of said object by said sum of predetermined continuous harmonics with said determined coefficients.

17. An X-ray examination system comprising:

the apparatus for reconstruction as claimed in claim 16;

an X-ray detector provided to produce the X-ray projection image data values; and a display unit for displaying object attenuation density values, wherein said apparatus for reconstruction is provided (i) to receive the X-ray projection image data values from said X-ray detector, and (ii) to supply data regarding the attenuation density of said object to said display unit.

18. A computer program product loadable into the internal memory of a computer, comprising software code portions for performing the method of claim 13 when said product is run on said computer.

* * * * *